(12) United States Patent
White et al.

(10) Patent No.: US 7,450,234 B2
(45) Date of Patent: Nov. 11, 2008

(54) CYLINDRICAL LENS-BASED LIGHT SENSOR AND USE OF THE SENSOR IN AN AUTOMATED METHOD AND APPARATUS FOR MONITORING A TARGET FLUID FOR CONTAMINANTS

(75) Inventors: Michael A. White, Arlington, MA (US); Christopher L. Templeman, Somerville, MA (US); Michael B. Frish, Andover, MA (US); Peter E. Nebolsine, Lincoln, MA (US)

(73) Assignee: Physical Sciences, Inc., Andover, MA (US)

( * ) Notice: Subject to any disclaimer, the term of this patent is extended or adjusted under 35 U.S.C. 154(b) by 221 days.

(21) Appl. No.: 11/264,744

(22) Filed: Nov. 1, 2005

(65) Prior Publication Data

US 2008/0002200 A1 Jan. 3, 2008

(51) Int. Cl.
*G01N 21/00* (2006.01)
(52) U.S. Cl. .................... 356/432; 356/339; 356/435
(58) Field of Classification Search ......... 356/339–343, 356/432, 435
See application file for complete search history.

(56) References Cited

U.S. PATENT DOCUMENTS 5,017,497 A * 5/1991 Gerard de Grooth et al. ..... 356/339
5,471,299 A * 11/1995 Kaye et al. .................. 356/336

OTHER PUBLICATIONS

"Optra Wins Contract for Particle Analyzer," Photonics Spectra, May 2004.
"Plant Materials and Equipment," Science & Technology, New Products, http://www.cen-online.org., date unknown.
"Low to Medium Turbidity Measurements—When Clarity Matters Most!," Ingold, Leading Process Analytics, Mettler Toledo, c. Mar. 2004.
"In-Line Aviation Fuel Monitor, "Autogrape,"" Physical Sciences Inc., Oct./Nov. 2003.
"Naval Advanced Fuel Diagnostics," Presented At: DESC Worldwide Fuels Conference Panel on Advanced Field Diagnostics on May 2, 2002., Richard A. Kamin, Naval Air Systems Command.
"Photonic Technology for Condition Based Monitoring," Physical Sciences Inc., Apr. 2003.
White, et al. "Photonic Sensors for Condition Based Monitoring," Physical Sciences Inc., MFPT Society Proceedings (In-House Cover), app. 2003.
"DoD News: Contracts Jun. 12, 2003," http://www.defenselink.mil/contracts/2003/c06122003_ct411-03.html.

* cited by examiner

*Primary Examiner*—L. G. Lauchman
*Assistant Examiner*—Iyabo S Alli
(74) *Attorney, Agent, or Firm*—Proskauer Rose LLP

(57) ABSTRACT

A light scattering sensor is provided with a cylindrical lens focusing received light along substantially parallel lines, or bands, that correspond to a range of scattering angles and a linear detector that detects the light intensity along the substantially parallel lines. By using a cylindrical lens, the lens serves as an auto-collimator, whereby light scattered at a specific angle from the collimated light beam strikes the linear detector at a corresponding specific location regardless of the location from where the light was scattered. Embodiments of the cylindrical lens-based light sensor can be applied to a number of different applications and industries that analyze light scattering intensity as a function of scattering angle. For example, embodiments of the cylindrical lens-based light scattering sensor can be used for monitoring a target fluid for contaminants.

29 Claims, 12 Drawing Sheets

CYLINDRICAL LENS-BASED LIGHT SENSOR AND USE OF THE SENSOR IN AN AUTOMATED METHOD AND APPARATUS FOR MONITORING A TARGET FLUID FOR CONTAMINANTS

GOVERNMENT RIGHTS

The government may have certain rights in the invention under Contract No. N68335-00-C-0384 from the United States Department of the Navy.

FIELD OF INVENTION

The present invention generally relates to light scattering measurements and processes in which the scattering behavior of particles or index of refraction variations between an optical source and a detector as a function of angle is required.

More particularly, the present invention relates to a light sensor having cylindrical optics to obtain high angular resolution of light scattering within an extended dynamic range and methods of using the sensor in applications that analyze light scattering intensity as a function of scattering angle.

BACKGROUND

The acquisition of light scattering profiles as a function of angle is a critical part of certain measurement devices used in many laboratory and industry settings. Typically, particle sizing devices for laboratory use in the various scientific fields utilize the optical performance at the focal point of a spherical lens illuminated by a collimated light source. In such configurations, scattering from a plane-wave source by index of refraction variations into other angles of propagation in relation to the optical axis of the spherical lens is collected into annular rings with radii increasing with scattering angle. The scattering profile is deduced in a couple of different ways.

According to a first method, a linear detector is placed at the focal point of the spherical lens and is configured to detect the light scattering along a radius line of the annular ring pattern. This method often suffers from the lack of spatial extent of the detector to reduce noise through averaging.

According to another method, a linear detector array is placed at the focal point of the spherical lens and is configured to acquire the entire ring pattern from which ring intensities are calculated using digital signal analysis. This method often suffers from the high cost of signal processing computation power.

Thus, there is a need for a light scattering sensor that is capable of obtaining high resolution scattering profiles within reasonable acquisition times and with sufficiently low noise to allow the determination of scattering profiles in the presence of weak scattering. There is also a need for such a sensor to be available inexpensively for common applications in commercial products.

SUMMARY OF THE INVENTION

According to one aspect of the invention, a light scattering sensor is provided with (i) a cylindrical lens focusing received light along substantially parallel lines, or bands, that correspond to a range of scattering angles and (ii) a linear detector that detects the light intensity along the substantially parallel lines. By using a cylindrical lens, the lens serves as an autocollimator, whereby light scattered at a specific angle from the collimated light beam strikes the linear detector at a corresponding specific location regardless of the location from where the light was scattered.

In particular embodiments, the cylindrical lens focuses the scattered light within a range of scattering angles such that the various scattering angles are mapped into vertical spatial bands at the detector. Preferably, the detector generates a video output of the bands. By virtue of this mapping of scattering angles to vertical bands, each pixel column of the video output converts directly to a given scattering angle, simplifying image analysis. A benefit of using a cylindrical lens is that commercial, rectangular Charge-Coupled Device (CCD) detectors can be used for significant savings in cost and manufacture complexity.

The linear detector can be a one dimensional (1D) linear detector or a two dimensional (2D) linear detector array having rows and columns. With a linear detector array, the detected light intensity can be computed as an average light intensity detected along the linear rows or columns of the detector array. In a preferred embodiment, the linear detector can output the detected light intensity in the form of a video signal that includes a line scan region representing the light intensity detected over a range of scattering angles.

Particular embodiments of the cylindrical lens-based light sensor can further include an optical filter disposed between the cylindrical lens and the linear detector, such that the optical filter can attenuate the intensity of the received light according to scattering angle or the intensity of the received light within regions in which the focused light deviates from alignment along substantially parallel lines. A benefit of such filtering is an increase in the range of light intensities that can be detected by the sensor.

According to another aspect of the invention, embodiments of the cylindrical lens-based light sensor can be applied to a number of different applications and industries that analyze light scattering intensity as a function of scattering angle.

According to one particular application, embodiments of the light scattering sensor can be used to monitor fluids that are utilized in many industrial processes. In many instances, the performance of such processes depends on the quality of the fluid. Manual fluid monitoring procedures have been developed to ensure the quality of various fluids, including fuels, lubricants, hydraulic fluids, and water. These procedures range from manual inspection to complex instrumentation for in-situ measurement.

For example, in military aircraft carriers, complex fuel distribution systems are installed for the purpose of refueling aircraft. Contaminated fuel has been known to cause engine failure, resulting in unnecessary repair work and delayed flights. Even very small quantities of dirt or solid matter can plug or restrict fuel metering orifices and accelerate the clogging of fuel filters.

Trained military personnel manually test between 200 and 400 fuel samples per day for the presence of contaminants, such as sediment and water. Approximately half of the samples are checked visually, while the other half are tested using known laboratory procedures involving wet chemistry techniques. Such manually intensive labor is extremely time consuming, costly and does not provide results in real time.

According to one embodiment, an automated method and apparatus is provided in which embodiments of the cylindrical lens-based light scattering sensor can be used for monitoring a target fluid for contaminants. Such an apparatus can include a light source directing a light beam across a target fluid, striking contaminants within the fluid causing the light beam to scatter; a first light sensor comprising (i) a cylindrical lens focusing received light along substantially parallel lines that correspond to a range of scattering angles and (ii) a linear detector detecting the intensity of the light along the substantially parallel lines; and a processing module capable of deriving a property of at least one of the contaminants within the target fluid from the detected light intensity. Such properties can include a concentration level of the contaminant in the fluid.

The first light sensor can further include an optical filter disposed between the cylindrical lens and the linear detector, such that the optical filter can attenuate the intensity of the received light according to scattering angle or the intensity of the received light within regions in which the focused light deviates from alignment along substantially parallel lines.

The linear detector can be a 1D or 2D detector array, such as a Charge Coupled Device (CCD) detector. In a 2D linear detector array, the detected light intensity can be computed as an average light intensity detected along the linear rows or columns of the array.

The processing module can (i) generate a statistical value that is characteristic of the light intensity detected within the range of scattering angles and (ii) derive a property of at least one of the contaminants within the target fluid from the statistical value. The statistical value can be a mean voltage level corresponding to a mean light intensity detected within the range of scattering angles.

According to a particular embodiment, the cylindrical lens-based light sensor can output the detected light intensity in the form of a video signal that includes a line scan region representing the light intensity detected within the range of scattering angles. In such embodiments, the processing module generates a set of values that are characteristics of the video signal that comprise (i) a mean voltage level from a portion of the line scan region of the video signal, (ii) a voltage level corresponding to a peak light intensity of the light beam, and (iii) a voltage level corresponding to a black level of the video signal. From these characteristics values, the processing module can derive, for example, a water concentration level within the target fluid from the mean voltage level that corresponds to a mean light intensity detected within the range of scattering angles, such that the mean voltage level is biased to the voltage level corresponding to the black level of the video signal and normalized to the voltage level of the peak light intensity of the light beam.

According to a particular embodiment, the cylindrical lens-based sensor detects light intensity within a range of substantially forward scattering angles relative to the orientation of the light beam. In such embodiment, the apparatus for monitoring a target fluid for contaminants can further include one or more discrete light scattering sensors that detect light intensity at discrete scattering angles over a period of time where the angles are substantially outside the range of the substantially forward scattering angles of the cylindrical lens-based light sensor. Accordingly, the processing module derives a property of at least one of the contaminants within the target fluid from the light intensity detected at the discrete scattering angle and from the light intensity detected within the range of substantially forward scattering angles.

For example, where the first light sensor outputs the detected light intensity in the form of a video signal, the processing module generates a set of values that are characteristics of the light intensity detected at the discrete scattering angle, where the set of characteristics values comprises (i) a mean or standard deviation of the light intensity detected at the discrete scattering angle over time, (ii) a voltage level corresponding to a peak light intensity of the light beam from the video signal, and (iii) a voltage level corresponding to a black level of the video signal. From these characteristics values, the processing module can derive, for example, a sediment concentration level within the target fluid from the mean or standard deviation of the light intensity detected at the discrete scattering angle over time such that the mean or standard deviation is normalized to a voltage level corresponding to a black level of the video signal that is biased to the voltage level of the peak light intensity of the light beam.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

According to one aspect of the invention, a light scattering sensor is provided with a cylindrical lens focusing received light along substantially parallel lines, or bands, that correspond to a range of scattering angles and a linear detector that detects the light intensity along the substantially parallel lines. By using a cylindrical lens, the lens serves as an auto-collimator, whereby light scattered at a specific angle from the collimated light beam strikes the linear detector at a corresponding specific location regardless of the location from where the light was scattered.

Figure 1:
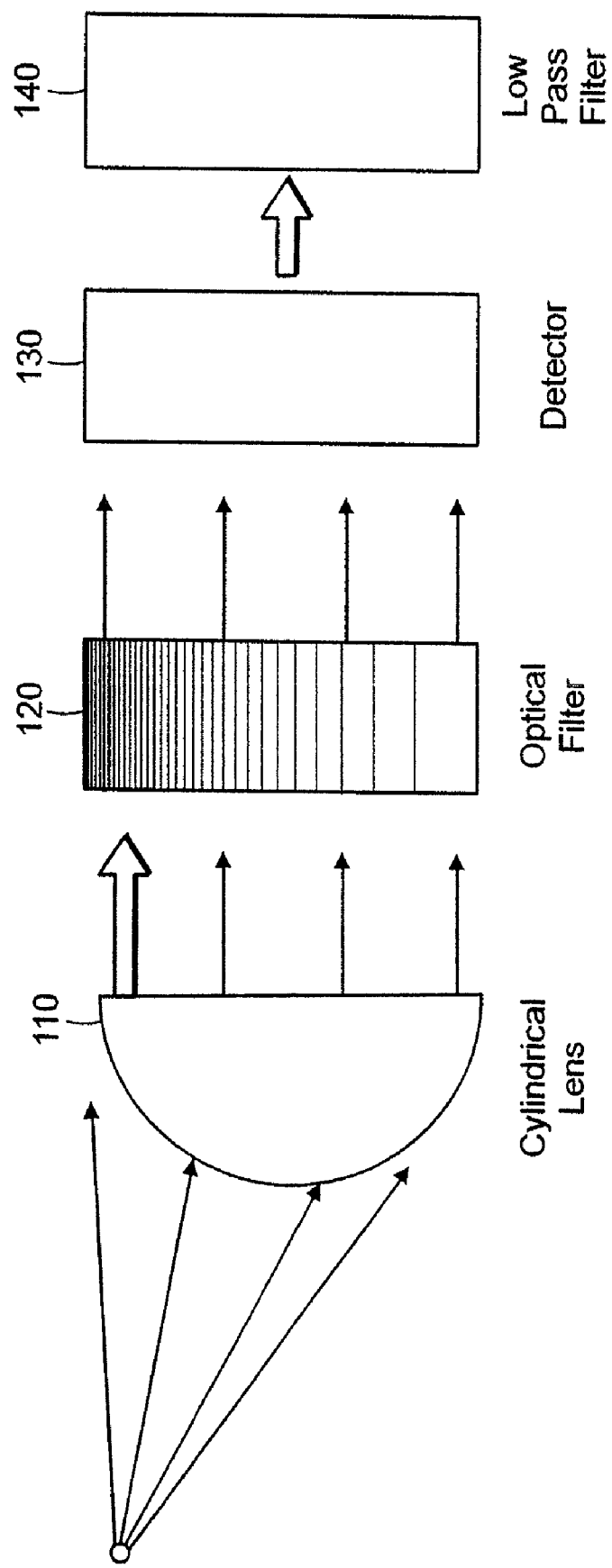
FIG. 1 is a schematic diagram of a cylindrical lens-based, light scattering sensor according to one embodiment.

FIG. 1 is a schematic diagram of a cylindrical lens-based, light scattering sensor according to one embodiment. The light scattering sensor 100 includes a cylindrical lens 110, an optical filter 120, a linear detector 130 and a low-pass filter 140. The cylindrical lens 110 is preferably positioned one focal length in front of the detector 130 and serves as an auto-collimator, whereby light scattered at a specific angle from the collimated light beam strikes the detector 130 at a corresponding specific location regardless of the location from where the light was scattered. The lens 110 focuses the scattered light within a range of scattering angles such that the various scattering angles are mapped into vertical spatial bands at the detector face. Preferably, the detector generates a video output of the bands. By virtue of this mapping of scattering angles to vertical bands, each pixel column of the video output converts directly to a given scattering angle, simplifying image analysis. A benefit of using a cylindrical lens is that commercial, rectangular Charge-Coupled Device (CCD) detectors can be used for significant savings in cost and manufacture complexity.

Once the incoming light passes through the lens 110 and is on the correct trajectories for angularly-resolved detection at the detector 130, the scattered/unscattered light preferably encounter the optical filter 120 (e.g., a photolithographic filter), which attenuates the light intensity depending on spatial location. Specifically, the incoming light is of much greater intensity at scattering angles about the unscattered beam than at the larger angles. By attenuating the light intensity levels at these angles, the dynamic detection range of the detector 130 can be increased such that weak intensity levels at the larger angular deviations can be detected.

Attenuation is gradually decreased such that light scattering at angles extending away from the unscattered beam can be detected. The optical filter 120 can also provide further attenuation to regions in which the focused scattered light deviates from alignment along substantially parallel lines. Preferably, the attenuation pattern, or filter function, of the photolithographic filter is engineered to prevent loss of the scattering information necessary for the desired property (e.g., concentration, particle size determination, etc.), while keeping the entire signal within the dynamic range of the filter. This filter function is determined using computer simulations of light scattering from particles in the same size range for which the device is intended (generally 1 to 500 microns).

Following the photolithographic filter 120 the photons impinge on the linear detector 130, preferably a Charge Coupled Device (CCD) detector. According to a particular embodiment, a profile analyzer having prior knowledge of the filter attenuation function can interpret the scattering signal to yield particle size information.

A simple pass filter 140 (e.g., 3 kHz) effectively smoothes the video output signal to yield the column averages, which, as described above correspond to scattering angles when a cylindrical lens focuses the scattered light onto the detector. Following the filter 140, the CCD video output signal is digitized at around 100 kHz effectively capturing the smooth scattering function. An analog-to-digital (A/D) converter providing 16-bit sampling can be used.

A benefit of using a cylindrical lens and high-resolution filter is that commercial, rectangular CCD detectors can be used for large cost savings. In other words, the lens and filter combination of FIG. 1 avoids the need to design custom CCD detectors for circular or ring detectors. Furthermore, image analysis is simplified, because pixel columns (or rows) of the CCD detector now convert directly to a given scattering angle, set by the focal length of the lens used. Thus, a benefit of the cylindrical lens-based, light scattering sensor of FIG. 1 and measurement devices that utilize this sensor is high angular resolution of light scattering at a much lower cost.

Figure 2A:
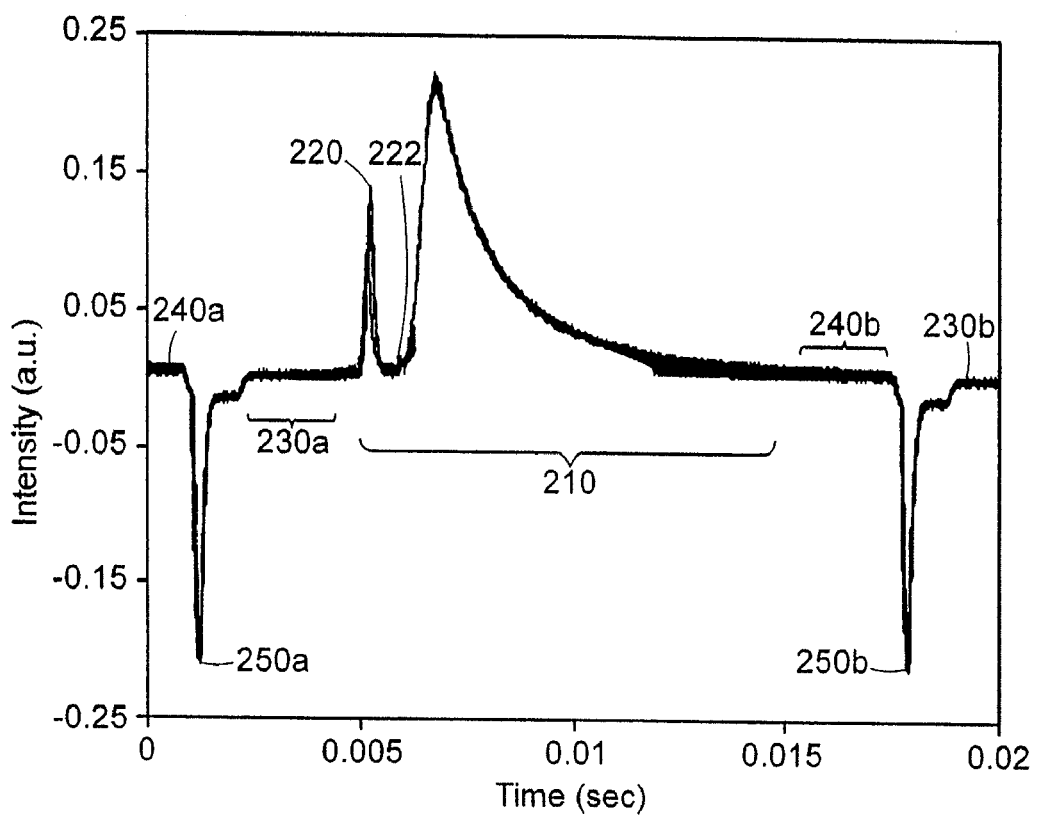
FIG. 2A is a diagram illustrating an example of a light scattering profile generated from the cylindrical lens-based, light scattering sensor according to the embodiment of FIG. 1.

FIG. 2A is a diagram illustrating an example of a light scattering profile generated from the cylindrical lens-based, light scattering sensor according to the embodiment of FIG. 1. Specifically, this profile is an example of a smoothed video output signal 200 from the sensor.

According to one embodiment, the video output signal is an NTSC (National Television Standards Committee) formatted RS-170 signal that is characterized by a horizontal line scan region 210 that is preceded by a short non-active period. During this period, a horizontal sync signal (HSYNC) 250 is sent between two short blanking periods, so-called front porch 230 and back porch 240.

The line scan region 210 represents the average voltage level that is proportional to the light intensity detected at each pixel column of a row of video output. By using a cylindrical lens to focus the light along substantially parallel lines, each pixel column of the pixel row also corresponds to an angle within the range of scattering angles. Thus, the line scan region 210 represents the average light intensity distributed over the range of scattering angles. This range can depend on the focal length between the lens and the detection capability of the CCD detector 130.

Within the line scan region 210, peak signal 220 is the average voltage level that is proportional to the intensity of the unscattered and preferably attenuated laser beam impinging on the CCD detector 130 through the cylindrical lens 110 and optical filter 120. The height of the laser peak 220 can be determined using software that can identify the location of the laser peak from the smoothed video output signal and then search for the top of the peak. Other methods known to those skilled in the art can be utilized for determining the laser peak height.

The signal depression 222 is due to the application of strong attenuation of the light intensity at angles near the unscattered beam. The front porch and back porch blanking intervals 230, 240 can be used as a reference level to remove DC components from the floating (AC-coupled) video signal.

Figure 2B:
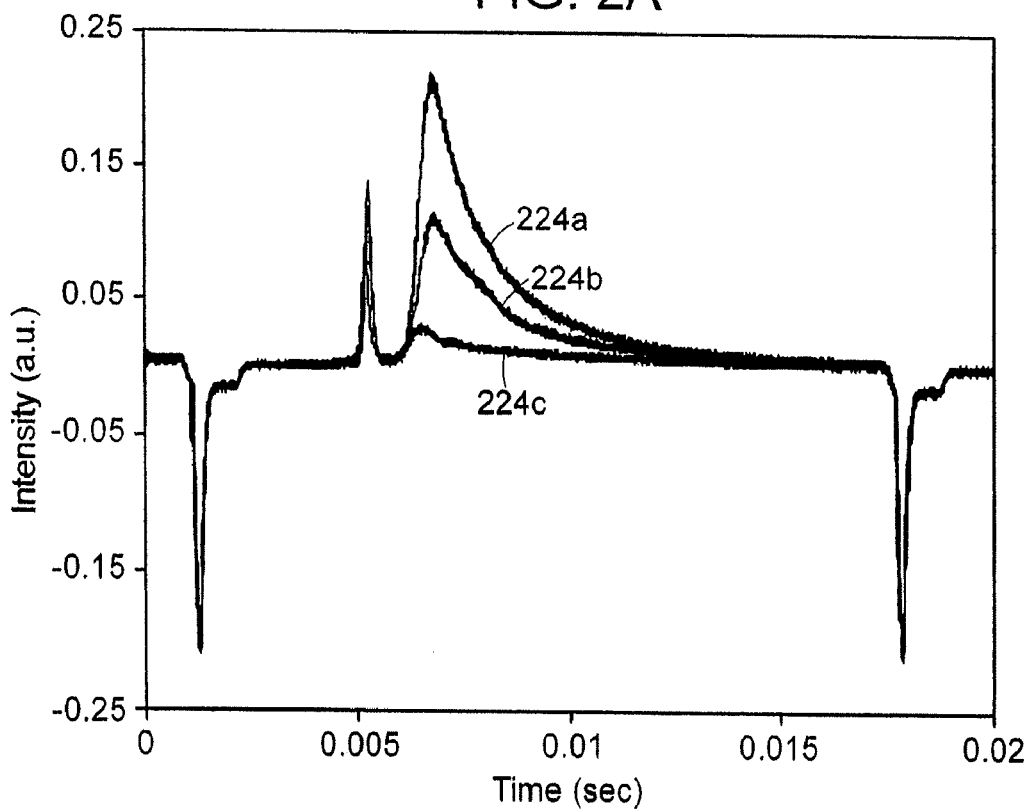
FIG. 2B is a diagram of several superimposed examples of light scattering profiles generated from the cylindrical lens-based, light scattering sensor according to the embodiment of FIG. 1.

FIG. 2B is a diagram of several superimposed examples of light scattering profiles generated from the cylindrical lens-based, light scattering sensor according to the embodiment of FIG. 1. As the type and concentration of a particular contaminant changes, the detected light scattering profiles also change. For example, the light scattering profiles 224a corresponds to a target fluid being contaminated with contaminant concentration that is greater than the free water concentrations that correspond to the respective light scattering profiles 224b, 224c. Thus, embodiments of the invention identify particular characteristics of the light scattering profiles that are sensitive to variations in contaminant type and concentration.

According to another aspect of the invention, embodiments of the cylindrical lens-based light scattering sensor 100 can be applied to a number of different applications and industries that analyze light scattering intensity as a function of scattering angle.

According to one particular embodiment, an automated method and apparatus is provided to monitor a target fluid for contaminants. Specifically, the method and apparatus analyze light scattering profiles due to the scattering of a collimated light beam striking contaminants within a target fluid. From these light scattering profiles, a contaminant index value is generated for each contaminant of interest and used to correlate against a predetermined reference to detect contaminant type and concentrations. The contaminant index value is preferably calculated from statistical values representing one or more light scattering profiles.

A light scattering sensor that utilizes a cylindrical lens is provided to reduce manufacture complexity and cost. Embodiments of the light scattering sensor can obtain high-resolution scattering profiles with preferably rapid acquisition times, but with sufficiently low noise to allow the determination of scattering profiles in the presence of weak scattering. The light scattering sensor can be used in a variety of applications and industries.

Figure 3:
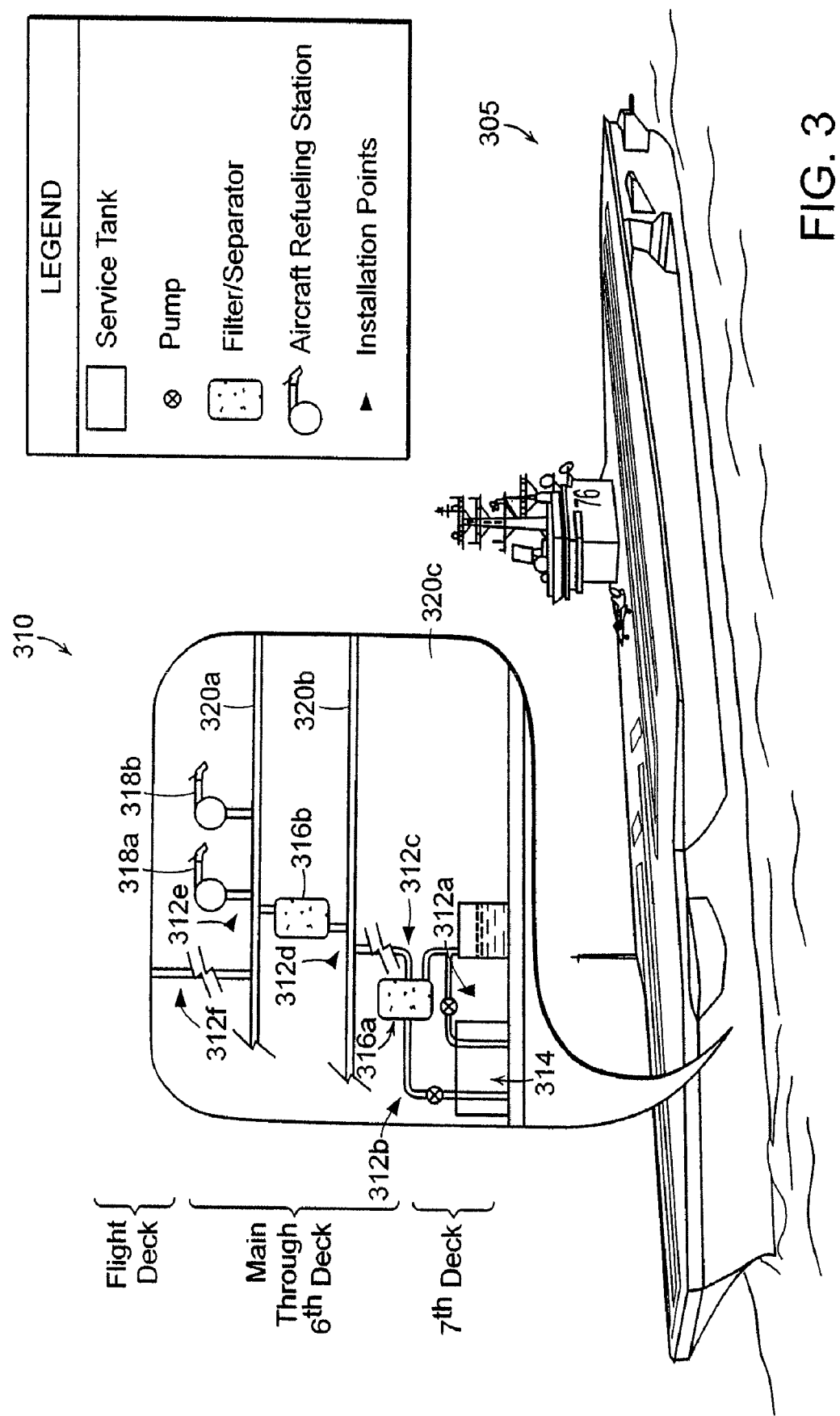
FIG. 3 is a diagram that illustrates a particular fuel distribution system of a modern aircraft carrier in which embodiments of the invention can be applied.

FIG. 3 is a diagram that illustrates a particular fuel distribution system of a modern aircraft carrier in which embodiments of the invention can be applied. The fuel distribution system 310 is vertically distributed through consecutive decks 320 of the aircraft carrier 305. Fuel is pumped through several filtration stages 316 from a service tank 314 to a number of aircraft refueling stations 318. The filtration stages 316 are intended to remove contaminants from the fuel stream, such as water and sediment. Sediment can include dust, dirt, rust and other such colloidal matter.

According to particular embodiments, in-line fluid contaminant monitors are located at positions 312a through 312f along the fuel distribution pipeline to detect types and concentrations of targeted contaminants entrained within the fuel stream. Although not so limited, these monitors can perform detection of sediment concentration levels between 0-10 mg/L with ±0.5 mg/L uncertainty in parallel with detection of free water concentration levels between 0-20 ppm with ±0.5 ppm uncertainty. Depending on the application, other contaminant types and characteristics, such as size, can be determined.

In this illustrated embodiment, the fluid contaminant monitors are located at positions 312a-312f along the fuel distribution pipeline 314 such that the fuel stream can be monitored at the inlets and outlets of each filtration stage 316. This monitor arrangement enables isolation of filtration failures when contaminant levels exceed set thresholds. However, other monitor arrangements can be implemented with different numbers of monitors in use.

Figure 4:
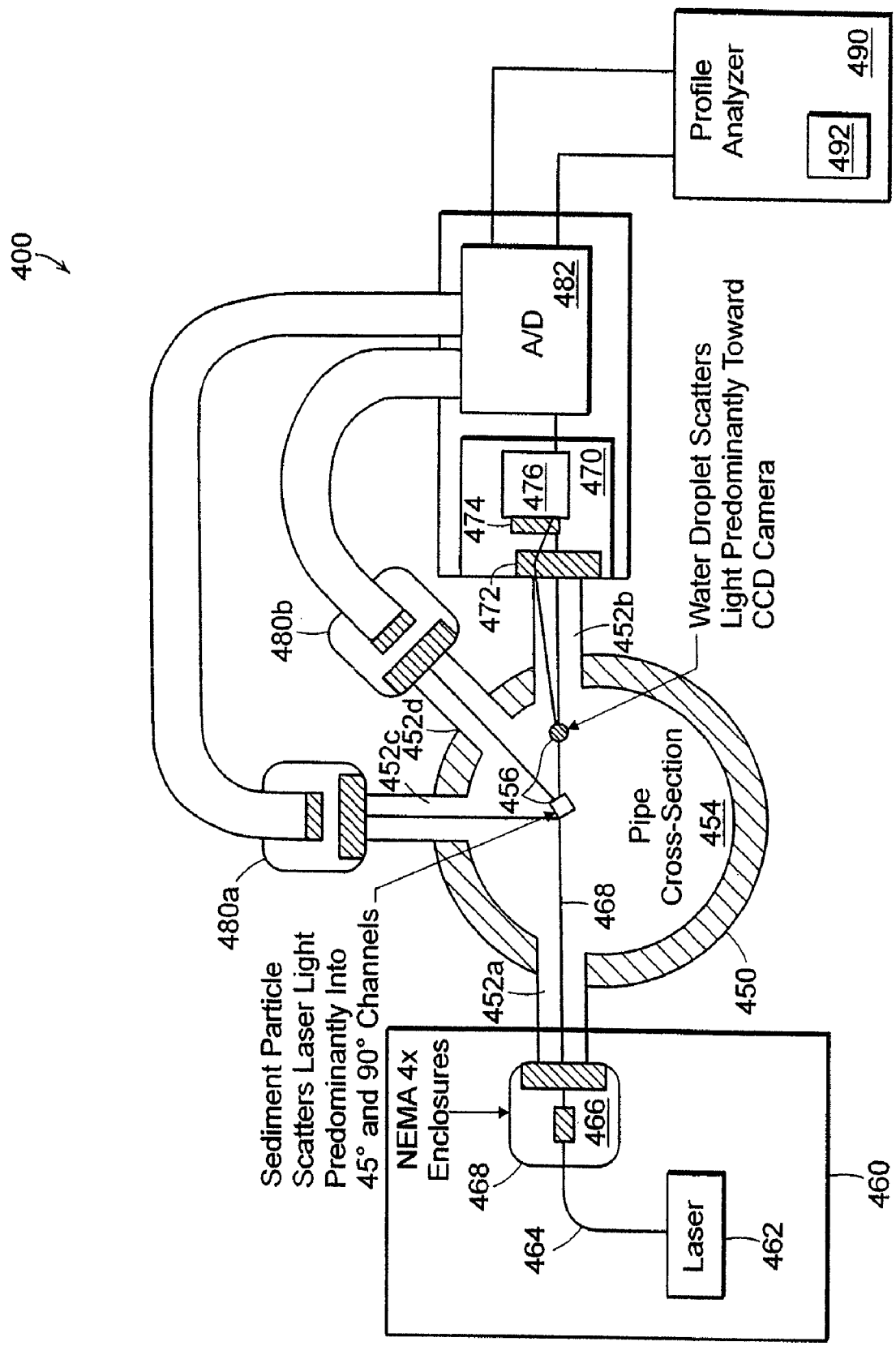
FIG. 4 is a diagram of an in-line fluid contaminant monitor according to one embodiment.

FIG. 4 is a diagram of an in-line fluid contaminant monitor according to one embodiment. In the illustrated embodiment, the monitor apparatus 400 is coupled to a section of a pipe conduit 450 through which the fuel 454 can flow. The monitor apparatus 400 includes a collimated light source 460, an arrangement of light-scattering sensors 470, 480a, 480b, and a profile analyzer 490.

The light source 460 directs a collimated light beam 468 through a windowed aperture 452a into the fuel sample 454 across the pipe conduit 450. The light source 460 can be a laser 462 (e.g., HeNe laser) that is coupled through an optical fiber 464 to standard focusing optics 466 that are housed in a NEMA 4× enclosure 468. As the beam of light traverses the fuel sample, the beam strikes contaminants 456 causing a portion of the collimated light beam to scatter along various scattering angles.

The arrangement of light-scattering sensors 470, 480a, 480b, through windowed apertures 452b-452d gather information about the angular distribution of the scattered light, which can be utilized to determine the type, concentration or other properties of targeted contaminants within the fluid flow. Each of the sensors 470, 480 generates a light scattering profile that represents the intensity of the detected light as a function of scattering angle. The angular distribution of the scattered light depends on the physical characteristics of the contaminants, including their dimensions and complex refractive indices. Scattering theory dictates that smaller particles (e.g., sediment) tend to generate omni-directional scattering patterns, while larger particles (e.g., free water droplets) tend to generate more forward scattering patterns with less side or back scattering.

Specifically, the cylindrical lens-based, light scattering sensor 470 detects scattered light over a range of forward scattering angles in substantially parallel lines or bands and outputs a light scattering profile in the form of a video output where each pixel column corresponds directly to a given scattering angle. The range of forward scattering angles corresponds to relatively small angular deviations with respect to the orientation of the direct path of the collimated light beam. For example, the range can include forward scattering angles between 0 and 10 degrees. Large spherical particulates, such as free water droplets, can be detected over this range.

According to one embodiment, the forward light scattering sensor 470 includes an arrangement of a cylindrical lens 472, an optical filter 474 and a detector 476. The range of the forward scattering angles can be more or less depending on the position of the lens 472 relative to the detector 476 and the surface size of the detector. In this illustrated embodiment, the cylindrical lens-based, forward light scattering sensor 470 opposes the light source 460 at a distance between 2 and 15 cm.

Light scattering sensors 480a, 480b are photodetectors that are coupled to the fluid conduit 450 at discrete angular locations of 45 and 90 degrees relative to the orientation of the direct path of the light beam 468. Discrete sensors 480a, 480b detect light scattering from small particles, such as sediment, or from irregularities in larger particles which cause them to scatter in omni-directional patterns. The output of the sensors 480a, 480b is a discrete, high angle light scattering profile in the form of a light-proportional voltage as a function of time.

The exact angular location of the discrete sensors 480a, 480b is irrelevant as long as the sensors can detect weak light scattering at large angles. For example, discrete sensors 480a, 480b can be positioned at 30 and 315 degrees respectively to obtain similar information. Either or both sensors 480a, 480b can be implemented and utilized in the monitor apparatus 400. In particular embodiments, discrete sensors 480a, 480b are silicon photodiode detectors having a single detection surface of approximately 2×2 mm.

Analog-to-Digital (A/D) circuitry 482 samples the light scattering profiles from the cylindrical lens-based sensor 470 and discrete sensors 480 prior to forwarding to the profile analyzer 490. According to one embodiment, the profiles are sampled at a rate of 100 kHz.

The profile analyzer 490 is a processing module capable of deriving a property of one or more contaminants within the target fluid from detected light intensity. Other embodiments of a processing module known to those skilled in the art can also be implemented.

According to the illustrated embodiment, the profile analyzer 490 obtains the light scattering profiles from the cylindrical lens-based sensors 470 and the discrete sensors 480 to generate a set of values that are characteristics of the light scattering profiles. The set of characteristics values can include values that are measured, extracted or derived from the scattering profiles. For example, the set of characteristics values can include statistical values that are particularly sensitive to contaminant type, concentration or other property, thus enabling a strong correlation between the detected light scattering profiles and actual contaminant types and such properties. From the set of profile characteristic values, the profile analyzer 490 derives a contaminant index value for each of the contaminant types of interest. For each contaminant type, the corresponding contaminant index value is correlated to a concentration level using a predetermined calibration reference 492.

Figure 5A:
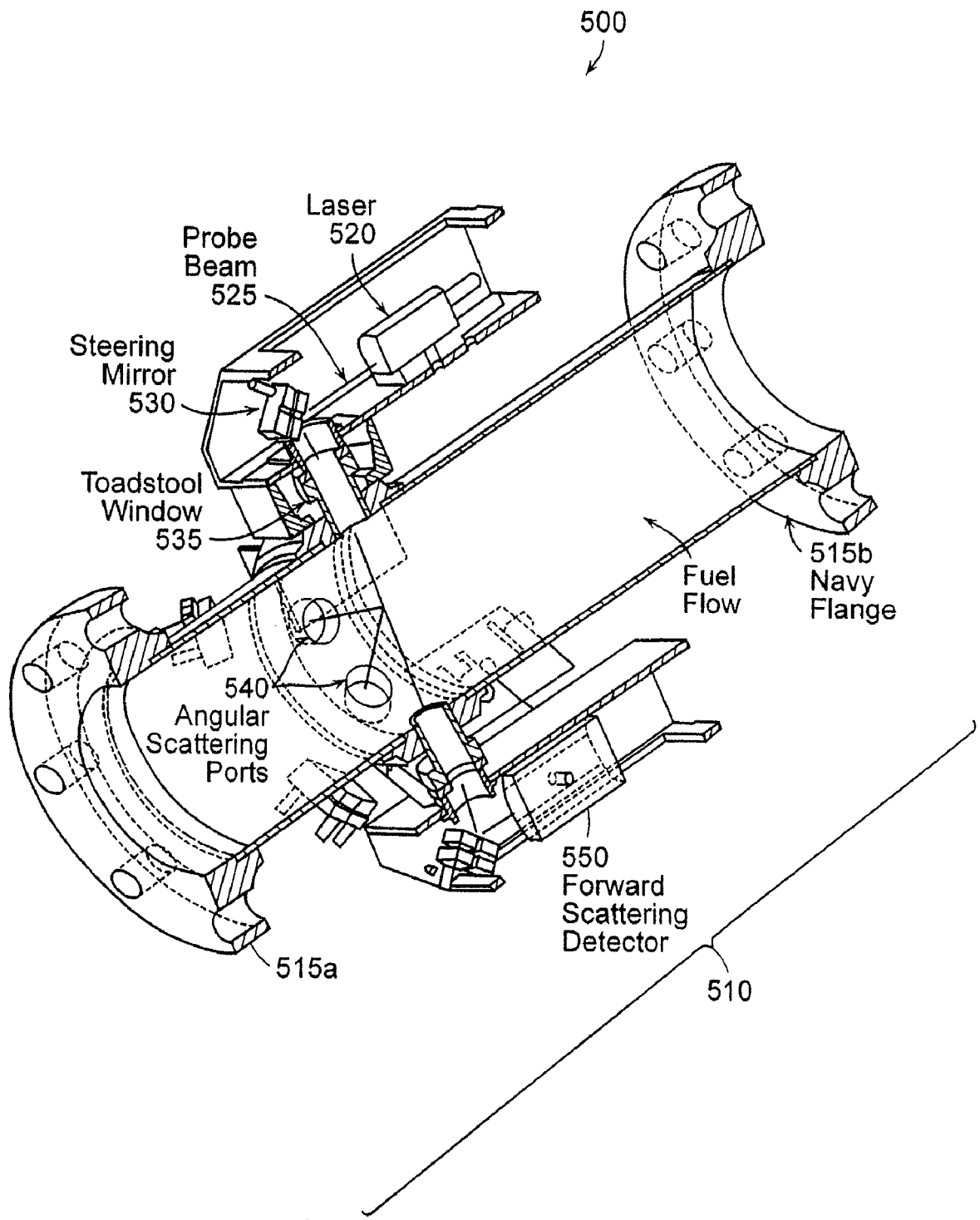
FIGS. 5A and 5B are diagrams of an in-line fluid contaminant monitor according to a particular embodiment.
Figure 5B:
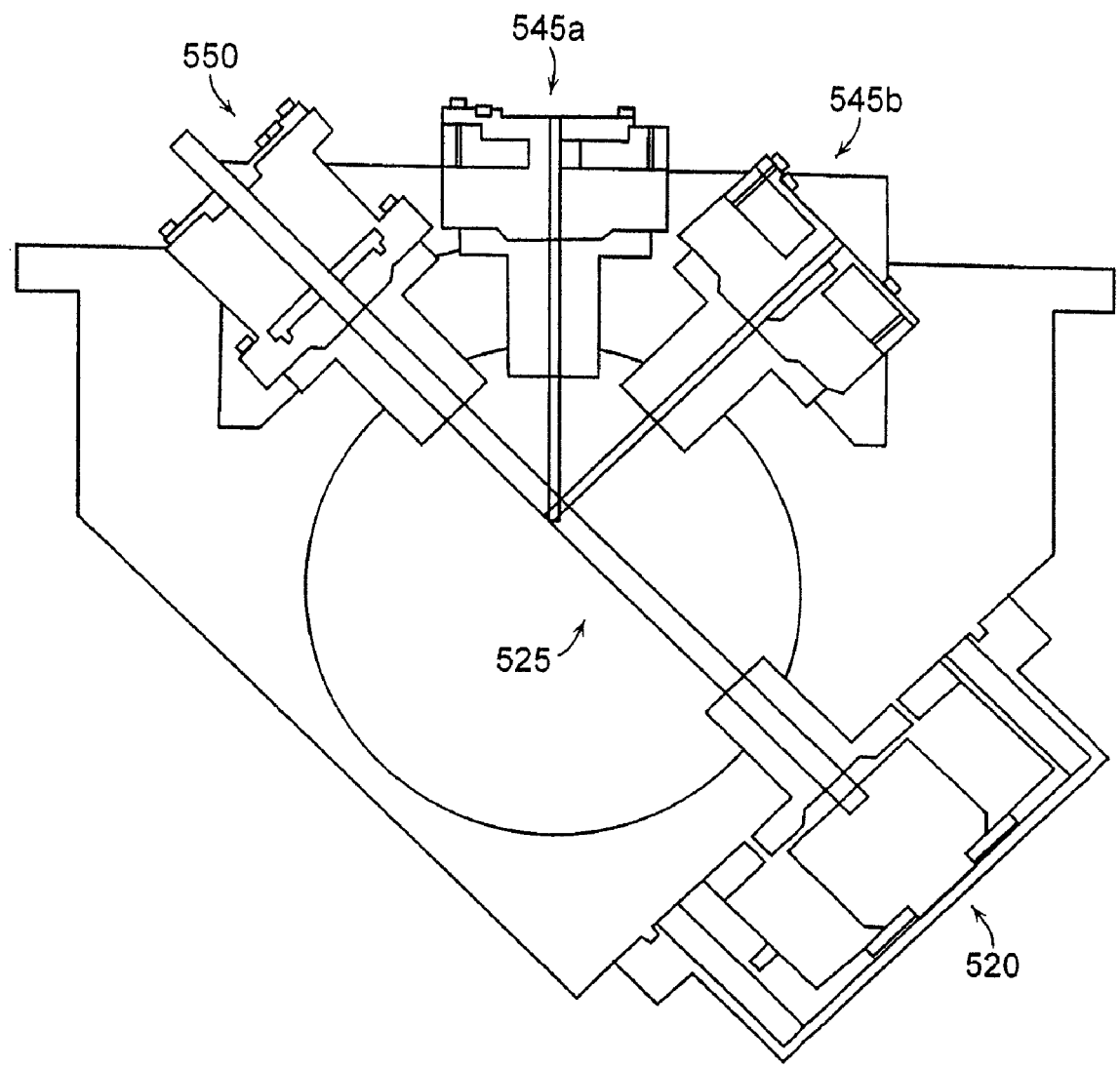

FIGS. 5A and 5B are diagrams of an in-line fluid contaminant monitor according to a particular embodiment. The monitor apparatus 500 is constructed in the form of a pipe section 510 having a flange 515a, 515b at each end for insertion within a preexisting fuel distribution pipe line. The monitor apparatus 500 includes a laser 520 that directs a probe beam 525 into the target fuel flow via a steering mirror 530 and a toadstool window 535. As the probe beam 525 traverses across the pipe section 510, it strikes contaminants entrained within the fuel flow causing portions of the probe beam 525 to scatter. The cylindrical lens-based, forward light scattering sensor 550 detects forward light scattering over a range of forward scattering angle, such as 0-10 degrees. According to one particular embodiment, the cylindrical lens-based sensor is constructed as illustrated in FIG. 1 to produce a forward light scattering profile in the form of a smoothed video output signal 200 as shown in FIGS. 2A and 2B.

Angular scattering ports 540 provide a windowed aperture through which one or more discrete, high angle light scattering sensors 545a, 545b can detect omnidirectional light scattering at a relatively large angular deviation (e.g., 45/90 degrees). According to one embodiment, discrete photodetectors are Avalanche Photodiodes (APD).

Figure 6:
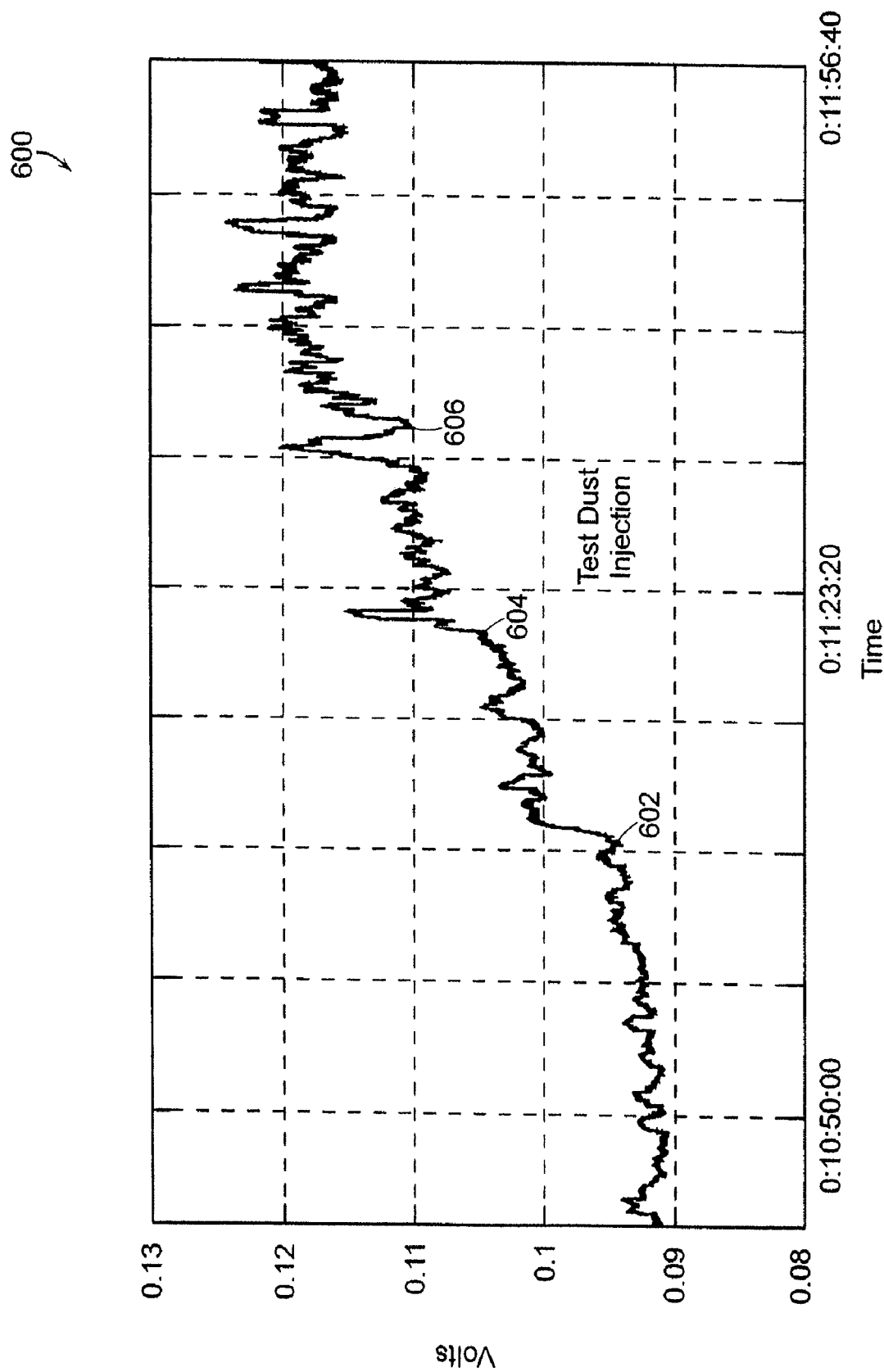
FIG. 6 is a diagram of an exemplary discrete high angle scattering profile in the form of a light-proportional voltage over a period of time according to one embodiment.

FIG. 6 is a diagram of an exemplary discrete, high angle scattering profile in the form of a light-proportional voltage over a period of time according to one embodiment. The profile 600 illustrates a trend in which the light-proportional voltage increases as the concentration level of sediment increases. Specifically, sediment is introduced into the fluid stream at time points 602, 604, and 606 causing the collimated light beam to scatter in an omni-directional pattern. As shown, the scattered light intensity detected by sensor 80a at 90 degrees increases as the concentration of sediment increases. Conversely, as the sediment is filtered out of the target fluid, the voltage level decreases back to a baseline voltage (e.g., 0.09 volts in this example).

Figure 7:
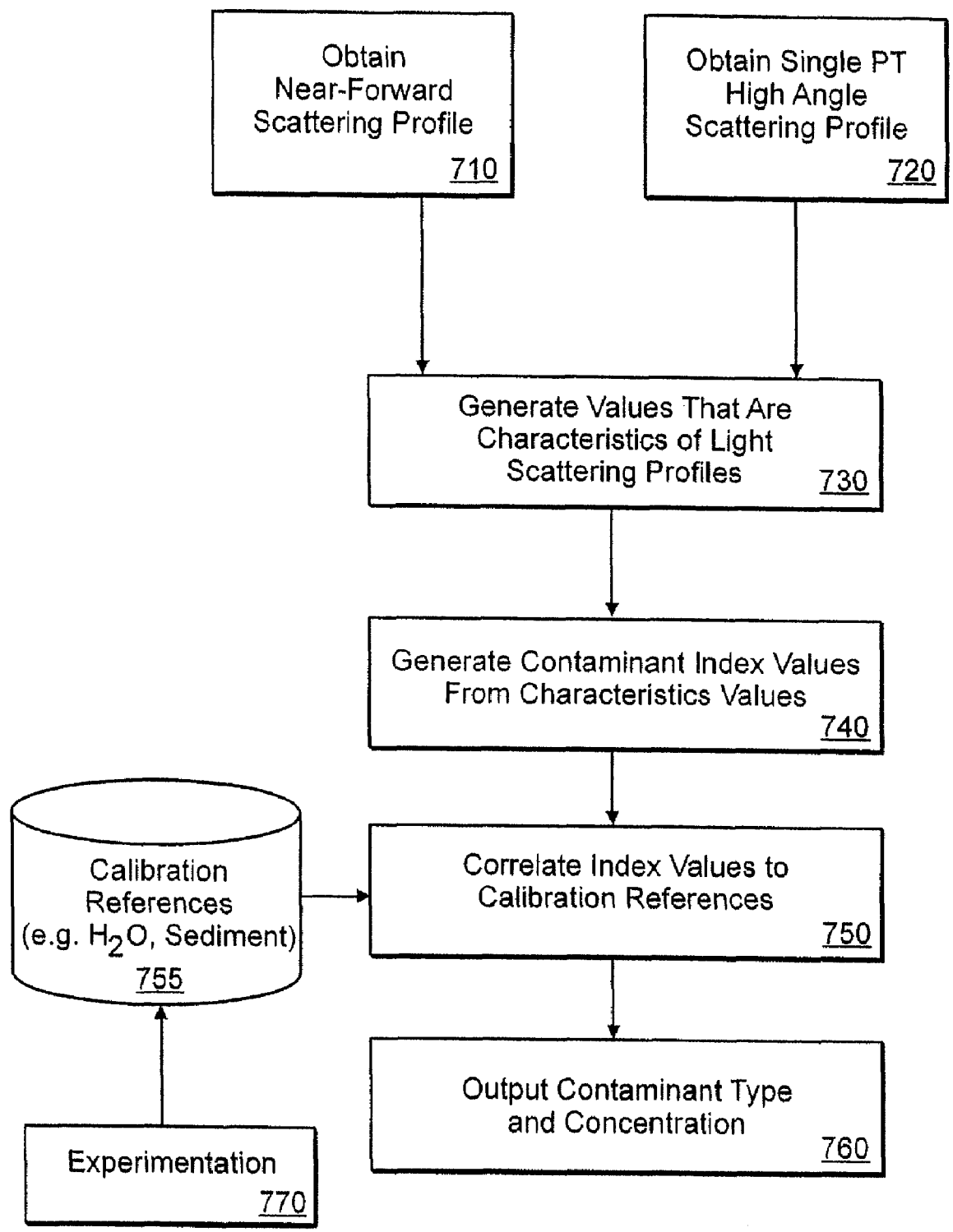
FIG. 7 is a flow chart illustrating a method for monitoring a target fluid for contaminants according to one embodiment.

FIG. 7 is a flow chart illustrating a method for monitoring a target fluid for contaminants according to one embodiment. At steps 710 and 720, respectively, the forward light scattering profile of the cylindrical lens-based sensor 470 and the discrete, high angle scattering profile of sensor 480a are obtained by the profile analyzer 490. Each of the profiles represents scattered light intensity as a function of one or more scattering angles. As previously discussed, the forward scattering profile can be in the form of a smooth video output signal, while the high-angle scattering profile can be in the form of a light-proportional voltage over time. For purposes of example, the forward scattering profile of FIG. 2A and the discrete, high angle scattering profile of FIG. 6 are referred to herein.

At step 730, the profile analyzer 490 generates values that are characteristics of the light-scattering profiles. There are a number of characteristic values that can be generated from the forward and high angle scattering profiles 200, 600. As the type and concentration of a targeted contaminant changes, the detected light scattering profile also change. Thus, embodiments of the invention identify particular characteristics of the light scattering profile that are sensitive to variations in contaminant type and concentration.

The shape of the forward light scattering profile 200 of FIG. 2A can be represented using data from the line-scan region 210, front porch region 230 and back porch region 240. As shown in FIG. 2B, as the concentration level increases, the intensity of forward scattering increases across the scattering angles. Conversely, as concentration levels decrease, the intensity of forward scattering decreases across the scattering angles. Thus, a mean voltage level can be calculated by the profile analyzer 490 from the line scan region 210 to represent changes in the distribution of forward light scattering in response to changes in concentration level of a targeted contaminant.

Characteristics such as laser peak height, front porch black level and back porch black level are also characteristic values of the video output signal that can affect the accuracy of the detected intensity values of the line scan region 224. Specifically, the CCD laser peak height is the voltage value on the smooth CCD video output signal that corresponds to the top of the peak which results from the direct laser impinging on the CCD detector 130 through the lens 110 and optical filter 120.

The front porch black level is another region selected from the digitized, smooth CCD output. It corresponds to a "non-detection" region in the CCD output. It provides a nearly light independent baseline for the CCD levels used.

A back porch black level is another region selected from the digitized, smooth CCD video output signal. It corresponds to a region at the very end of the scattering profile where the scattered light can land if scattering into 8 degrees occurs. This is useful for normalizing the forward light scattering profile where shape is the important concern, not overall level. Therefore, back porch black level provides another baseline.

Other characteristics values, including statistical values, may be measured, extracted or derived from the profile.

Regarding the discrete, high angle scattering profile 600 of FIG. 6, as sediment is introduced into the fluid flow stream, the light-proportional voltage levels detected correspond to an increase in the amount of omni-directional scattering and thus an increase in the concentration of sediment levels. Conversely, as the sediment is removed from the targeted fluid, the light-proportional voltage levels decrease. Thus the profile analyzer 490 can generate a statistical value that is characteristic of the light intensity detected at a high angle (e.g., 90 degrees) over time. Mean voltage level and standard deviation relative to a baseline voltage are characteristic values of this profile that are sensitive to content type and concentration levels. Other characteristics values, including statistical values, may be measured, extracted or derived from the profile.

At step 740, the profile analyzer 490 generates a contaminant index value for each of the target contaminants from the characteristic values of the light-scattering profiles.

For example, with respect to sediment contamination, the contaminant index value can be based on the standard deviation voltage level of the discrete, high angle scattering profile, in which the standard deviation is derived from the light proportional voltage levels over a specified time period (e.g., 1000 sampled points of FIG. 6).

According to a particular embodiment, the contaminant index value for sediment is derived from the standard deviation of the light-proportional voltage normalized to the voltage level of the laser peak height 220 that is biased to the front porch black level 230 of the forward light scattering profile of FIG. 2A. In other words, the contaminant index value (CIV) for sediment contamination can be described by Equation (1):

$$\text{CIV}_{sediment} = (\text{standard deviation voltage level @90 degrees})/(\text{laser peak height} - \text{front porch black level}) \quad (1)$$

The contaminant index value for sediment contamination can be derived from other statistical values, including mean voltage levels, that are sensitive to contaminant type and concentration levels.

With respect to free water contamination, the contaminant index value can be based on a mean voltage level of the forward light scattering profile in which the mean voltage level is derived from the average voltage levels of the pixel columns for a pixel row within the line-scan region 210. As previously discussed, when a cylindrical lens is used in conjunction with a CCD detector that produces a video output, the pixel columns also correspond directly to scattering angles. Thus, the mean voltage level represents the average light intensity over the range of forward scattering angles. As shown in FIG. 2B, the mean voltage level can increase or decrease with the contaminant type and concentration.

According to a particular embodiment, the contaminant index value for free water is derived from the mean voltage level from the line scan region 210, which is biased to the laser peak height 220 and normalized to the back porch black level 240. In other words, the contaminant index value (CIV) for free water contamination can be described by Equation (2):

$$CIV_{water} = (\text{mean voltage level} - \text{back porch black level})/(\text{laser peak height} - \text{back porch black level}) \quad (2)$$

The contaminant index value for free water contamination can also be derived from other statistical values that are sensitive to contaminant size and concentration levels.

At step 750, the contaminant index values are correlated to calibration references 735 that correspond to respective contaminant types (e.g., water, sediment). The calibration reference 735 can be a functional relationship between the calculated index value and predetermined concentration levels for a target contaminant that is determined through experimentation as discussed with respect to step 770. The calibration reference can also be a lookup table in which calculated index values are mapped to a specific concentration level for that contaminant.

At step 760, the profile analyzer 490 outputs the contaminant type that was detected and a corresponding concentration level of that contaminant within the fluid flow. Based on this output, additional processing can be performed such as generating an alert when the concentration level of the targeted contaminant exceeds a set threshold.

At step 770, the calibration references 755 are predetermined through experimentation. Specifically, for a sample of contaminated fluid, a contamination index value can be mapped to a manual measurement of a particular contaminant concentration level or other property. According to one embodiment, the experimentation procedure involves introducing a sample amount of a particular contaminant into a target fluid flow system. A manual method for measuring concentration levels of the target contaminant is conducted. For example, in the case of fuel samples, the American Society for Testing and Materials (ASTM) has established standard laboratory procedures for detecting water and sediment in fuel samples. Specifically, ASTM D2276 defines the standard test method for particulate contamination in aviation fuel by line sampling, and ASTM D3240 defines standard test method for undissolved water in aviation turbine fuels, the entire contents of which are incorporated herein by reference.

In parallel, steps 710 through 740 of FIG. 7 are conducted resulting in a derived contaminant index value. This contaminant index value is then mapped to the manually determined concentration level of the targeted contaminant. This process is repeated for different concentrations of the targeted contaminant such that a number of contaminant index values are mapped to different concentration levels of the targeted contaminant.

Figure 8A:
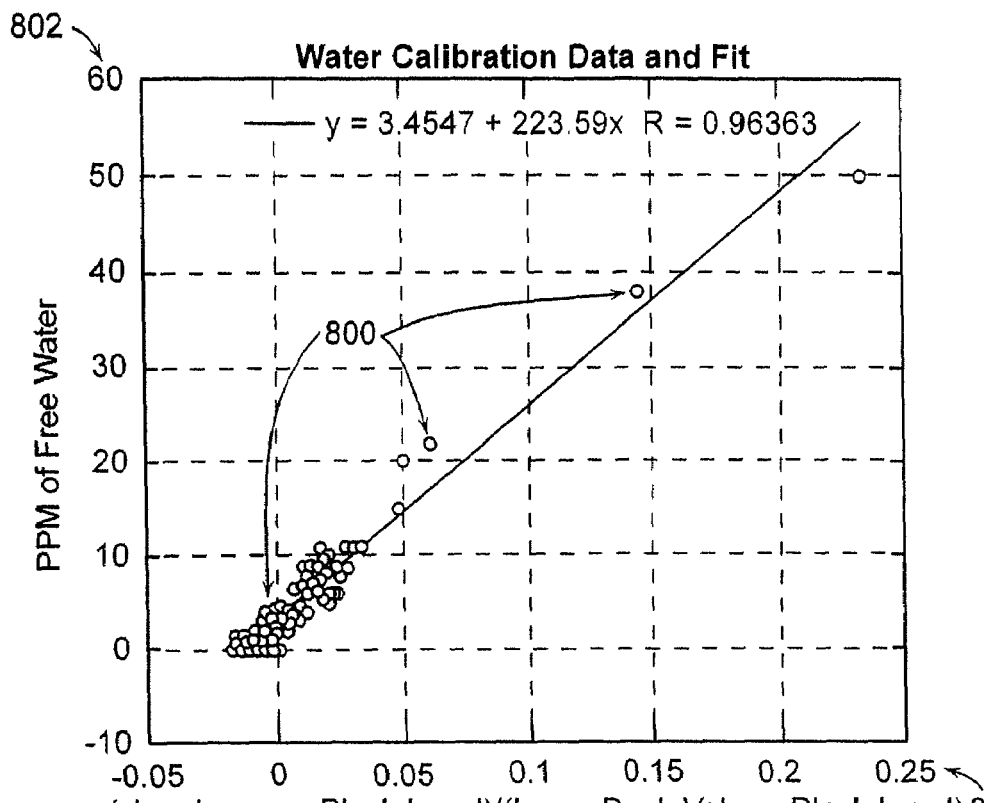
FIGS. 8A and 8B are diagrams that each illustrate a collection of points that map measured concentrations to the calculated contaminant index values for particular contaminant types.
Figure 8B:
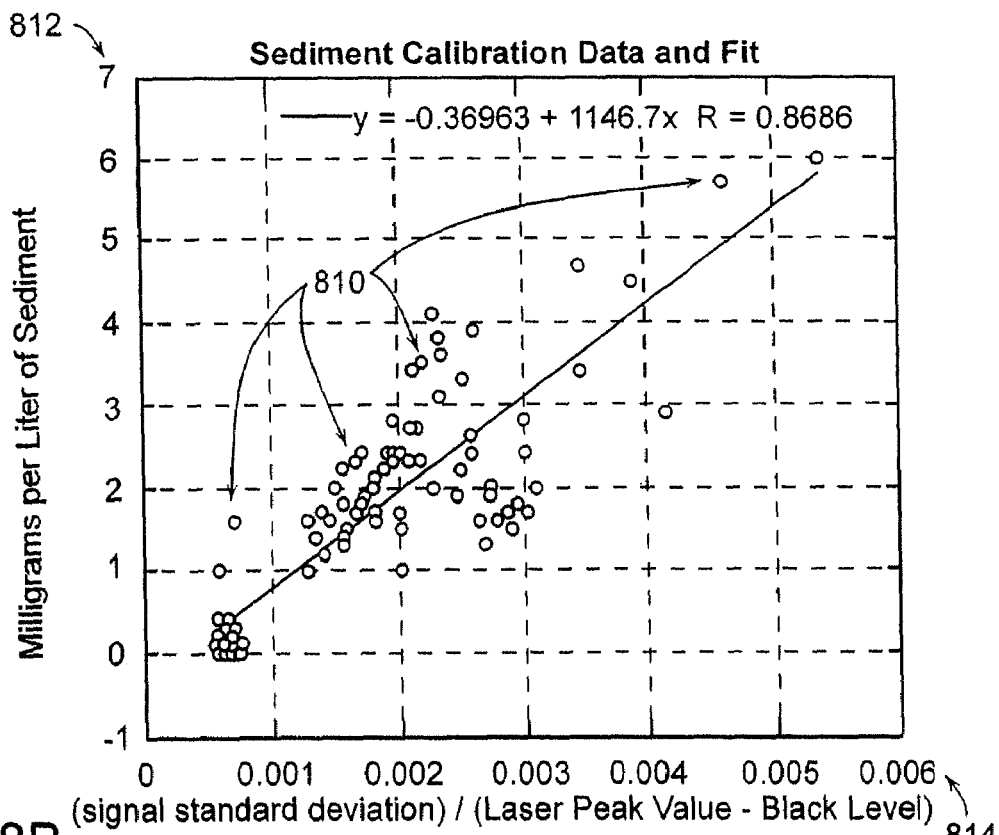

For example, FIG. 8A is a diagram illustrating a collection of points 800 that map measured concentrations 802 to the calculated contaminant index values 804 for free water contamination. Likewise, FIG. 8B is a diagram illustrating a collection of points 810 that map measured concentrations 812 to the calculated contaminant index values 814 for sediment contamination.

By plotting a sufficient number of points that correlate actual concentrations to contamination index values, an equation can be fit to the collection of points using, for example, a least squares fitting such that for any contaminant index value a corresponding concentration level for a particular contaminant can be output. For example, with respect to FIG. 8A, the equation for computing free water contamination from light intensity is:

$$y = 3.4547 + 223.59x \quad (3)$$

where y is the Free Water Contamination in parts per million (PPM); and x is the calculated contamination index for free water.

With respect to FIG. 8B, the equation for computing sediment contamination from light intensity is:

$$y = -0.36963 + 1146.7x \quad (4)$$

where y is sediment contamination in milligrams per liter; and x is the calculated contamination index for sediment.

Figure 9A:
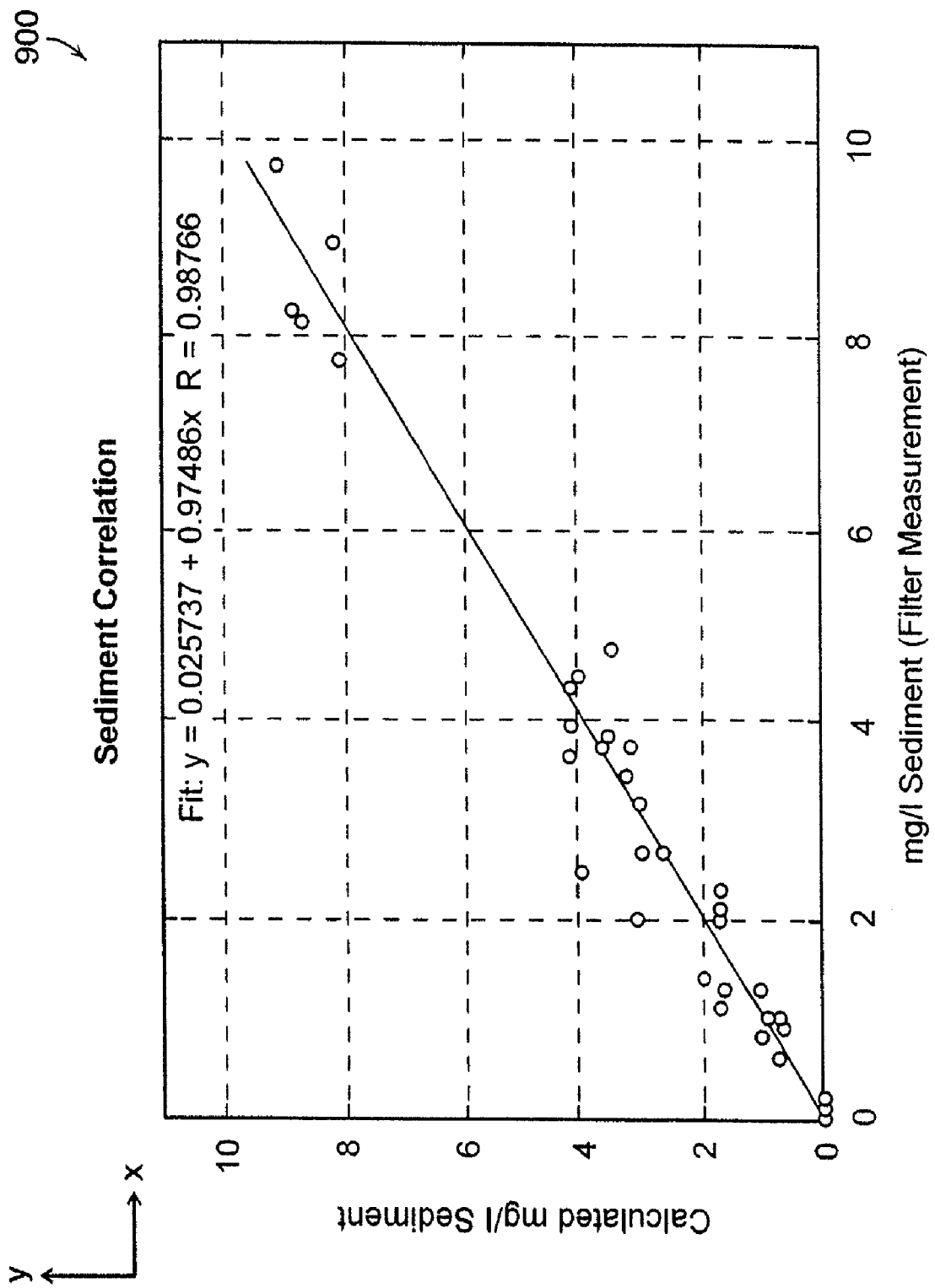
FIGS. 9A and 9B are comparison charts illustrating the correlation of the concentration levels for sediment and free water as determined by manual means and the concentration levels determined according to embodiments of the invention.
Figure 9B:
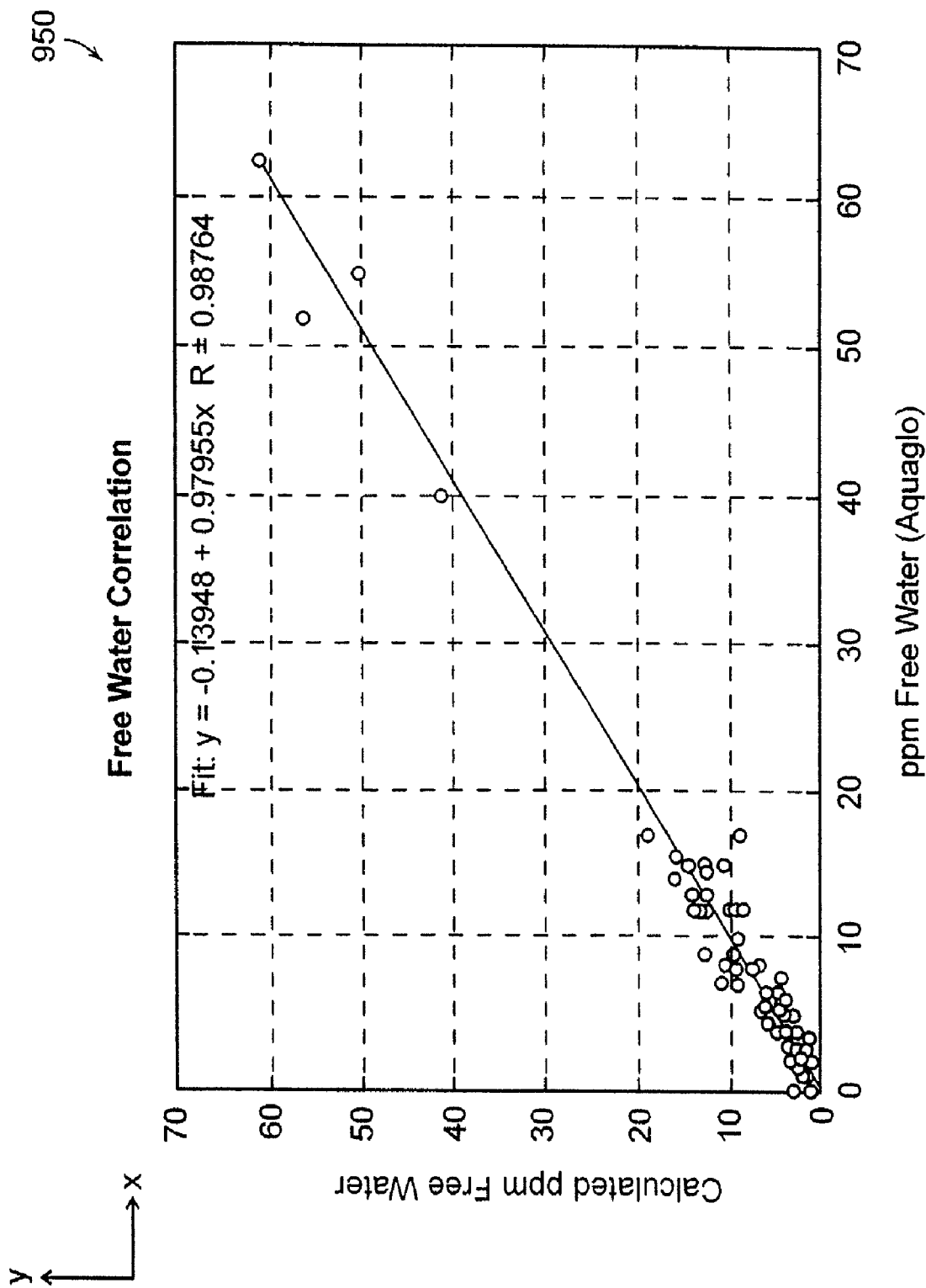

FIGS. 9A and 9B are comparison charts illustrating the correlation of the concentration levels for sediment and free water, respectively, as determined by manual means and the concentration levels determined according to embodiments of the invention. As shown, the contaminant concentration levels determined by both means correlate substantially to a one-to-one ratio.

For example, in FIG. 9A, the sediment concentration levels that are calculated from the correlation of concentration index values are plotted along the Y-axis of the comparison chart 900, while the sediment concentration levels determined through a manual filtration measurement are plotted along the X-axis. The calculated concentration values and the measured concentration values for sediment have a linear correspondence in which the slope of this linear function is approximately equal to one.

Similarly, in FIG. 9B, the free water concentration levels that are calculated from the correlation of concentration index values are plotted along the Y-axis of the comparison chart 950, while the free water concentration levels determined through a manual measurement are plotted along the X-axis. The calculated concentration values and the measured concentration values for free water also have a linear correspondence in which the slope of this linear function is approximately equal to one.

Figure 10:
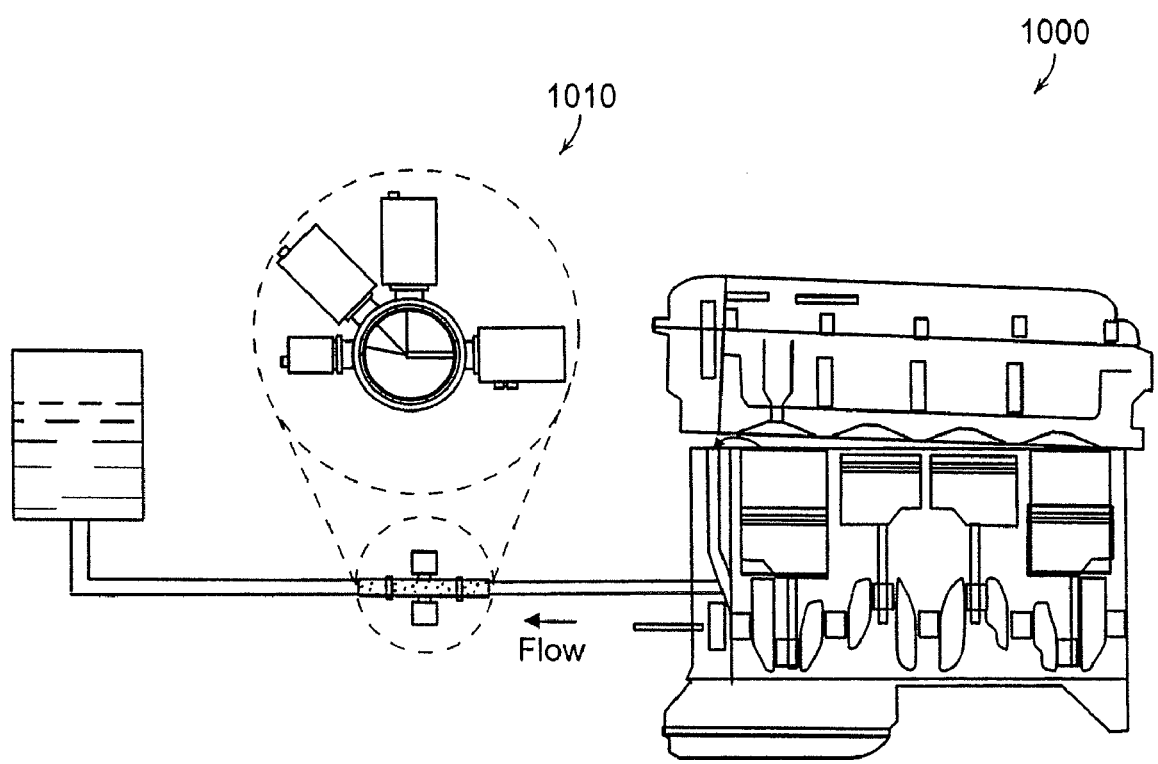
FIG. 10 is a schematic diagram of an engine coolant system in which embodiments of the monitor apparatus can be implemented.

Although the previous example refers to a particular application in which the in-line fluid contaminant monitor is used for monitoring sediment and water in a fuel pipeline of a fuel distribution system, one can appreciate that other embodiments of the fluid contaminant monitor can be applied to many types of industrial applications that require detection of individual concentration levels of constituent contaminants entrained within a target fluid. For example, FIG. 10 is a schematic diagram of an engine coolant system 1000 in which embodiments of the monitor apparatus 1010 can be implemented.

While this invention has been particularly shown and described with references to preferred embodiments thereof, it will be understood by those skilled in the art that various changes in form and details may be made therein without departing from the scope of the invention encompassed by the appended claims.

What is claimed is:

1. A light scattering sensor comprising:
   a linear detector comprising a detector face that detects light intensity; and a cylindrical lens focusing scattered light to strike the detector face as a plurality of substantially parallel bands of light, each of the plurality of substantially parallel bands of light striking the detector face corresponding to a specific scattering angle of the scattered light.

2. The sensor of claim 1 further comprising:
an optical filter disposed between the cylindrical lens and the linear detector, the optical filter attenuating the intensity of the scattered light according to the specific scattering angle.

3. The sensor of claim 1 further comprising:
an optical filter disposed between the cylindrical lens and the linear detector, the optical filter attenuating the intensity of the scattered light within regions in which the focused light deviates from alignment along substantially parallel bands of light.

4. The sensor of claim 1 wherein the linear detector outputs the detected light intensity in the form of a video signal that includes a line scan region representing the light intensity detected over the range of scattering angles.

5. The sensor of claim 1 wherein the linear detector is a charge coupled device (CCD) detector.

6. The sensor of claim 1 wherein the linear detector is a detector array having linear rows and columns, the detected light intensity being an average of light intensity detected along the linear rows or columns of the detector array.

7. An apparatus for monitoring a target fluid for contaminants, comprising:
a light source directing a light beam across a target fluid, the beam striking contaminants within the fluid causing the light beam to scatter;
a first light sensor comprising (i) a linear detector comprising a detector face that detects light intensity and (ii) a cylindrical lens focusing scattered light within a range of scattering angles to strike the detector face as a plurality of substantially parallel bands of light, each of the plurality of substantially parallel bands of lights striking the detector face corresponding to a specific scattering angle of the scattered light; and
a processing module capable of deriving a property of at least one of the contaminants within the target fluid from the detected light intensity.

8. The apparatus of claim 7 further comprising:
an optical filter disposed between the cylindrical lens and the linear detector, the optical filter attenuating the intensity of the scattered light according to scattering angle.

9. The apparatus of claim 7 further comprising:
an optical filter disposed between the cylindrical lens and the linear detector, the optical filter attenuating the intensity of the scattered light within regions in which the focused light deviates from alignment along substantially parallel bands of light.

10. The apparatus of claim 7 wherein the linear detector is a charge coupled device (CCD) detector.

11. The sensor of claim 7 wherein the linear detector is a detector array having linear rows and columns, the detected light intensity being an average of light intensity detected along the linear rows or columns of the detector array.

12. The apparatus of claim 7 wherein:
the processing module (i) generates a statistical value that is characteristic of the light intensity detected within the range of scattering angles and (ii) derives a property of at least one of the contaminants within the target fluid from the statistical value.

13. The apparatus of claim 12 wherein the statistical value is a mean voltage level corresponding to a mean light intensity detected within the range of scattering angles.

14. The apparatus of claim 7 wherein the light sensor outputs the detected light intensity in the form of a video signal that includes a line scan region representing the light intensity detected within the range of scattering angles.

15. The apparatus of claim 14 wherein:
the processing module generates a set of values that are characteristics of the video signal, the set of characteristics values comprising (i) a mean voltage level from a portion of the line scan region of the video signal, (ii) a voltage level corresponding to a peak light intensity of the light beam, and (iii) a voltage level corresponding to a black level of the video signal;
the processing module derives a water concentration level within the target fluid from the mean voltage level that corresponds to a mean light intensity detected within the range of scattering angles, such that the mean voltage level is biased to the voltage level corresponding to the black level of the video signal and normalized to the voltage level of the peak light intensity of the light beam.

16. The apparatus of claim 7 wherein the range of scattering angles is a range of substantially forward scattering angles relative to the orientation of the light beam, the apparatus further comprising:
a discrete light scattering sensor that detects light intensity at a discrete scattering angle over a period of time, the discrete scattering angle being substantially outside the range of the substantially forward scattering angles; and
the processing module deriving a property of at least one of the contaminants within the target fluid from the light intensity detected at the discrete scattering angle and from the light intensity detected within the range of substantially forward scattering angles.

17. The apparatus of claim 16 wherein:
the first light sensor outputs the detected light intensity in the form of a video signal;
the processing module generates a set of values that are characteristics of the light intensity detected at the discrete scattering angle, the set of characteristics values comprising (i) a mean or standard deviation of the light intensity detected at the discrete scattering angle over time, (ii) a voltage level corresponding to a peak light intensity of the light beam from the video signal, and (iii) a voltage level corresponding to a black level of the video signal;
the processing module derives a sediment concentration level within the target fluid from the mean or standard deviation of the light intensity detected at the discrete scattering angle over time such that the mean or standard deviation is normalized to a voltage level corresponding to a black level of the video signal that is biased to the voltage level of the peak light intensity of the light beam.

18. A method of sensing scattered light, comprising:
detecting intensity of light at a detector face of a linear detector; and
focusing scattered light using a cylindrical lens to strike the detector face as a plurality of substantially parallel bands of light each of the plurality of substantially parallel bands of light striking the detector face corresponding to a specific scattering angle of the scattered light.

19. The method of claim 18 wherein the linear detector is a detector array having linear rows and columns, the detected light intensity being an average of light intensity detected along the linear rows or columns of the detector array.

20. A method of monitoring a target fluid for contaminants, comprising:

directing a light beam across a target fluid, the beam striking contaminants within the fluid causing the light beam to scatter;

detecting intensity of light at a detector face of a linear detector;

focusing scattered light within a range of scattering angles using a cylindrical lens to strike the detector face as a plurality of substantially parallel bands of light each of the plurality of substantially parallel bands of light striking the detector face corresponding to a specific scattering angle of the scattered light; and deriving a property of at least one of the contaminants within the target fluid from the detected light intensity.

21. The sensor of claim 20 wherein the linear detector is a detector array having linear rows and columns, the detected light intensity being an average of light intensity detected along the linear rows or columns of the detector array.

22. The method of claim 20 wherein deriving a property of at least one of the contaminants from the detected light intensity comprises:

generating a statistical value that is characteristic of the light intensity detected within the range of scattering angles; and deriving a property of at least one of the contaminants within the target fluid from the statistical value.

23. The method of claim 22 wherein the statistical value is a mean voltage level corresponding to a mean light intensity within the range of scattering angles.

24. The method of claim 20 further comprising generating a video signal that includes a line scan region representing the light intensity detected within the range of scattering angles.

25. The method of claim 24 wherein deriving a property of at least one of the contaminants from the detected light intensity comprises:

generating a set of values that are characteristics of the video signal, the set of characteristics values comprising (i) a mean voltage level from a portion of the line scan region of the video signal, (ii) a voltage level corresponding to a peak light intensity of the light beam, and (iii) a voltage level corresponding to a black level of the video signal;

deriving a water concentration level within the target fluid from the mean voltage level that corresponds to a mean light intensity detected within the range of scattering angles, such that the mean voltage level is biased to the voltage level corresponding to the black level of the video signal and normalized to the voltage level of the peak light intensity of the light beam.

26. The method of claim 20 wherein the range of scattering angles is a range of substantially forward scattering angles relative to the orientation of the light beam, the method further comprising:

detecting light intensity at a discrete scattering angle over a period of time, the discrete scattering angle being substantially outside the range of the substantially forward scattering angles; and deriving a property of at least one of the contaminants within the target fluid from the light intensity detected at the discrete scattering angle and from the light intensity detected within the range of substantially forward scattering angles.

27. The method of claim 26 further comprising:

generating a video signal that represents the light intensity detected within the range of scattering angles;

generating a set of values that are characteristics of the light intensity detected at the discrete scattering angle, the set of characteristics values comprising (i) a mean or standard deviation of the light intensity detected at the discrete scattering angle over time, (ii) a voltage level corresponding to a peak light intensity of the light beam from the video signal, and (iii) a voltage level corresponding to a black level of the video signal; and deriving a sediment concentration level within the target fluid from the mean or standard deviation of the light intensity detected at the discrete scattering angle over time such that the mean or standard deviation is normalized to a voltage level corresponding to a black level of the video signal that is biased to the voltage level of the peak light intensity of the light beam.

28. An apparatus for monitoring a target fluid for contaminants, comprising:

means for directing a light beam across a target fluid, the beam striking contaminants within the fluid causing the light beam to scatter;

means for detecting intensity of light comprising a detector face; and a cylindrical lens focusing scattered light to strike the detector face as a plurality of substantially parallel bands of light, each of the plurality of substantially parallel bands of light striking the detector face corresponding to a specific scattering angle of the scattered light; and means for deriving a property of at least one of the contaminants within the target fluid from the detected light intensity.

29. A light scattering sensor comprising:

means for detecting intensity of light comprising a detector face; and a cylindrical lens focusing scattered light to strike the detector face as a plurality of substantially parallel bands of light, each of the plurality of substantially parallel bands of light striking the detector face corresponding to a specific scattering angle of the scattered light.

* * * * *